(12) United States Patent
Yazawa et al.

(10) Patent No.: US 6,333,421 B1
(45) Date of Patent: Dec. 25, 2001

(54) CAPSAICINOIDE-LIKE SUBSTANCES HAVING ESTER BOND

(75) Inventors: Susumu Yazawa, Nagaokakyo; Tatsuo Watanabe, Shimizu; Tohru Fushiki, Otsu; Kenji Kobata, Shimizu; Masatake Imai, Yokohama; Yuko Setoguchi, Yokohama; Shuichi Hashizume, Yokohama, all of (JP)

(73) Assignee: Morinaga & Co., Ltd., Tokyo (JP)

( * ) Notice: Subject to any disclaimer, the term of this patent is extended or adjusted under 35 U.S.C. 154(b) by 0 days.

(21) Appl. No.: 09/623,598

(22) PCT Filed: Mar. 3, 1999

(86) PCT No.: PCT/JP99/00999

§ 371 Date: Oct. 23, 2000

§ 102(e) Date: Oct. 23, 2000

(87) PCT Pub. No.: WO99/44981

PCT Pub. Date: Sep. 10, 1999

(30) Foreign Application Priority Data

Mar. 4, 1998 (JP) .................................. 10-069542

(51) Int. Cl.$^7$ .................................. C07C 57/00
(52) U.S. Cl. .................. 554/229; 514/544; 514/885; 426/648
(58) Field of Search .............. 554/229; 514/885, 514/544; 426/648

Primary Examiner—Deborah D Carr
(74) Attorney, Agent, or Firm—Oblon, Spivak, McClelland, Maier & Neustadt, P.C.

(57) ABSTRACT

The purpose of the invention is to provide capsaicinoid-like substances to be used as food additives and pharmaceutical ingredients. Capsaicinoid-like substances represented by the following general formula:

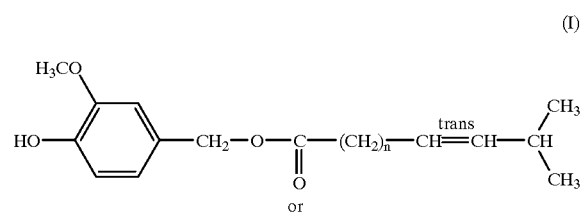

Figure 1:
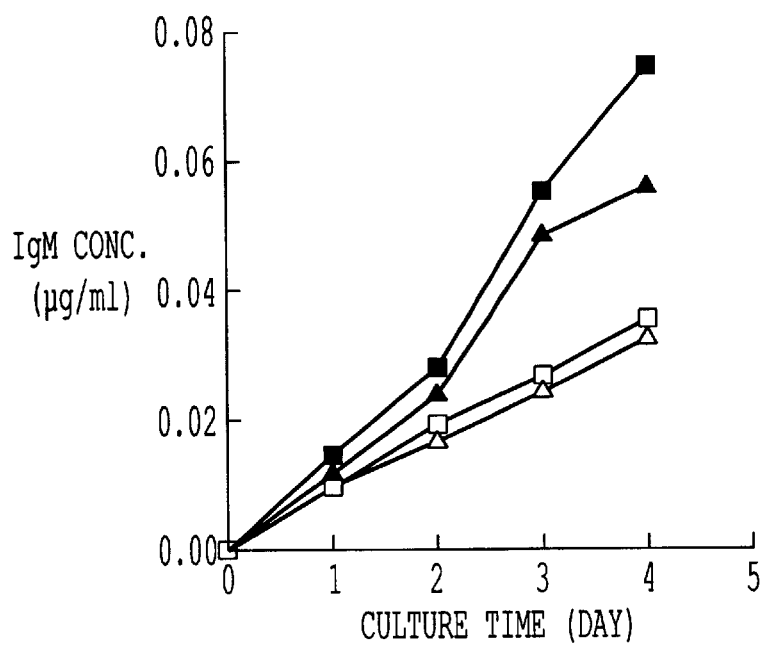

or and food and pharmaceutical compositions comprising them.

15 Claims, 3 Drawing Sheets

CAPSAICINOIDE-LIKE SUBSTANCES HAVING ESTER BOND

FIELD OF INVENTION

This invention relates to novel capsaicinoid-like substances with an ester linkage, and to a food and pharmaceutical compositions comprising said substances.

PRIOR ART

*Capsicum annuum L.* species, peppers, have been used worldwide as foods, spices and medicines. The major pungent components contained in them are capsaicin, (E)-N-[(4-hydroxy-3-methoxyphenyl)-methyl]-8-methyl-6-nonenamide, and dihydrocapsaicin, i.e., 6.7-dihydro derivative of capsaicin. Further, more than 12 other capsaicinoids have been found as minor pungent components such as nordihydrocapsaicin (that contains one less methylene group than dihydrocapsaicin), homocapsaicin (that contains one more methylene group than capsaicin) and homodihydrocapsaicin (that contains one more methylene group than dihydrocapsaicin).

Up to now, it has been found that capsaicin has many physiological activities such as promotion of adrenal catecholamine secretion so as to enhance the oxidation of fatty acids and to inhibit obesity (Buck, S. H.; Burks, T. F. , *Phamacol. Rev.*, 1986, 38, 179–226, Suzuki, T.; Iwai, K., *Chemistry and Pharmacology*, 1984, Vol.23, 1984, Szolcsanyi, J., *Handbook of Experimental Pharmacology*, Vol.60, 1982).

However, since capsaicin has a strong pungency and nociceptive activity, it can not be used in a large amount and its usage as a food additive or a drug is considerably limited.

Several studies have reported that several non-pungent capsaicinoids as well as capsaicin have physiological activities such as promotion or enhancement of adrenal catecholamine secretion (Watanabe, T.; Kawada, T.; Kato, T.; Harada, T.; Iwai, K., *Life Sci.*, 1994, 54, 369–374). Since these capsaicinoids have no pungent components, it may be expected that they may be used as food additives and pharmaceutical ingredients.

It has been reported that the fruits of a non-pungent fixed variety of pepper, named "CH-19 sweet" (an introduction number at Kyoto Univ., Agr. Dept., vegetables and horiculture laboratory) which had been selected and fixed from a pungent fixed variety of pepper, "CH-19", obtained in Thailand, contain only a small amount of capsaicinoids, but a considerable amount of capsaicinoid-like substances (CLSs) (Yazawa,S.; Suetome,N.; Okamoto,K.; Namiki,T., J. Japan Soc. Hort. Sci., 1989, 58, 601–607).

The present inventors have now tried a structural analysis of the capsaicinoid-like substances contained in the CH-19 sweet, and succeeded in their identification to complete the present invention.

SUMMARY OF THE INVENTION

The present invention relates to novel capsaicinoid-like substances represented by the following general formula:

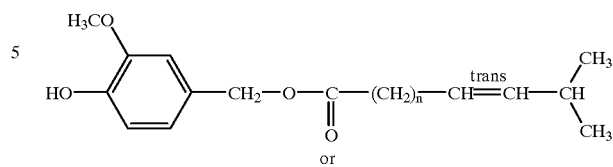

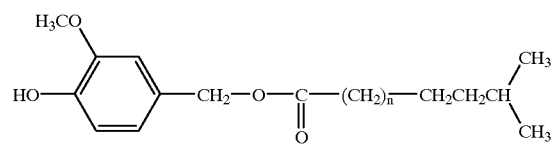

The present capsaicinoid-like substances (Formula I) are characterized in that they consist of a branched non-saturated fatty acid that is combined via an ester linkage with vanillyl alcohol, whereas the prior capsaicinoids consist of a branched non-saturated fatty acid that is combined via an amide linkage with vanillyl alcohol.

The present capsaicinoid-like substances (Formula II) are those whose fatty acid moiety has been saturated.

In these formulae, the value "n" is preferably 3, 4 or 5, the structural formulae wherein said value is 4 are shown as follows:

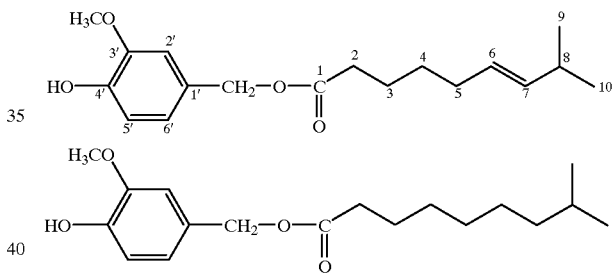

DETAILED EXPLANATION OF THE INVENTION

Since the present capsaicinoid-like substances have no pungency and substantially no cytotoxicity, they may be used as food additives or pharmaceutical ingredients that show a variety of physiological activities such as enhancing energy metabolism and potentiating an immune system.

Further, the present capsaicinoid-like substances have a possibility to be used as food additives or pharmaceutical ingredients for enhancing endurance capacity in continuous excises, or as a non-narcotic analgesic.

Accordingly, the present invention relates to a food composition comprising said capsaicinoid-like substances. The present food composition may take any form such as solid, liquid, sol, gel, powder and granule, and it may be prepared by any method known in the art.

An amount of the present capsaicinoid-like k contained in the food composition may be optionally determined by those skilled in the art, depending on the purpose of their formulation, and the kind, form and purpose of the food composition, and the like. For example, the capsaicinoid-like substances may be comprised in an amount of at least $10^{-5}\%$ by weight in chocolate.

It is not necessary to purify the present capsaicinoid-like substances to be comprised in the food composition. Thus, the food composition may comprise the non-pungent fixed variety of pepper, "CH-19" per se, its dried and pulverized material or its extract with various solvents that are conventionally used in the art, for example, ethyl acetate, alcohols such as ethanol, and emulsifiers used for food stuff.

The present invention relates to a pharmaceutical composition comprising said capsaicinoid-like substances as well. The present pharmaceutical composition may take any form known in the art, such as solution buffered with various salts and buffers, suspension, emulsion and the like.

Buffering salts include alkali and alkaline earth metal salts, phosphate and sulfate. For example, citrate, phosphate, HEPES, Tris-hydroxy aminomethane may be used in a physiologically acceptable concentration.

The present pharmaceutical composition may be formulated in any form in addition to the above liquid ones, such as tablet, powder, sol, gel, granule and an embedded one with liposome.

In formulation, any excipients and additives known in the art may be used in a pharmaceutically acceptable amount. The amount of the capsaicinoid-like substances comprised in the pharmaceutical composition may be optionally determined by those skilled in the art, depending on the properties of other ingredients, the purpose of use, the age and weight of a patient, and effects required, and the like.

The present pharmaceutical composition may be administered by various routes depending on its formulation, form and the like, such as orally, intraveneously, subcutaneously, intramuscularly, intraperitonealy, pharyngonasally, etc.

SUMMARIZED EXPLANATION OF DRAWINGS

[FIG. 1]

It shows the effect of the present capsaicinoid-like substances (designated as "CLS-B") on IgM antibody production of hybridoma H8. In the figure, ▲ and ■ represent the values obtained in a culture medium supplemented with 100 $\mu$M and 20 $\mu$M of CLS-B, respectively. On the other hand, □ and Δ represent the values obtained in a culture medium supplemented with 100 $\mu$M and 20 $\mu$M of capsaicin, respectively.

[FIG. 2]

It shows the effect of the present capsaicinoid-like substances (designated as "CLS-B") on IgG antibody production of hybridoma S97. In the figure, ▲ and ■ represent the values obtained in a culture medium supplemented with 100 $\mu$M and 20 $\mu$M of CLS-B, respectively. On the other hand, □ and Δ represent the values obtained in a culture medium supplemented with 100 $\mu$M and 20 $\mu$M of capsaicin, respectively.

[FIG. 3]

It shows the effect of the present capsaicinoid-like substances (designated as "CLS-B") on viability of hybridoma S97. In the figure, ▲ and ■ represent the values obtained in a culture medium supplemented with 100 $\mu$M and 20 $\mu$M of CLS-B, respectively. On the other hand, □ and Δ represent the values obtained in a culture medium supplemented with 100 $\mu$M and 20 $\mu$M of capsaicin, respectively.

[FIG. 4]

It shows the change in the temperature of skin and eardrum due to the intake of the dried and pulverized "CH-19 sweet". A vertical line shows the change of temperature and a horizontal line shows time course (min) after intake.

[FIG. 5]

It shows the change in the temperature of mice body after the feeding of the present capsaicinoid-like substances in an amount of 50 mg per 1 kg body weight into mice.

BEST MODE FOR CARRYING OUT THE PRESENT INVENTION

The present capsaicinoid-like substances may be prepared by isolation and purification from the non-pungent fixed variety of pepper, "CH-19 sweet", or may be chemically synthesized by a known method based on the structural formulae in this specification. One of the present compound may be easily synthesized by a well-known esterification using 8-methyl nonanoate (8-methyl pelargonoate) and vanillyl alcohol as starting material.

The present invention will be illustrated in more detail with the following examples which, however, should not be construed to limit the scope of the present invention in any way.

EXAMPLE

Example 1

Isolation and Purification of the Present Capsaicinoid-like Substances

After fresh fruits (1.00 kg) of CH-19 sweet had been freeze-dried, their seeds and calyces were removed, and the residue was extracted with 1.8 L each of ethylacetate three times by use of a Universal Homogenizer (Nihon Seiki Seisakusho, Japan). The ethylacetate extract was evaporated under reduced pressure to distill out ethylacetate and to afford an oleoresin (7.3 g). The oleoresin was chromatographed on silica gel (Silica gel 60 Merck; 36×200 mm) with stepwise elution of n-hexane and ethylacetate. The fraction eluted with ethylacetate was rechromatographed on reversed phase silica gel (Wakosil 25C18 of Wako Pure Chem. Co. Ltd. (Japan): 20×50 mm) with 75% MeOH eluent to afford Compound 3 (4.5 mg)

On the other hand, the fraction eluted with n-hexane/ ethylacetate (80:20) was rechromatographed on reversed phase silica gel (Wakosil 25C18 of Wako Pure Chem. Co. Ltd. (Japan); 20×90 mm) with 75% MeOH eluent. And a mixture containing Compound 1 was obtained, and the following fraction gave Compound 2 as a colorless oil (59.7 mg).

The mixture containing Compound 1 was rechromatographed on reversed phase silica gel (Wakosil 25C18 of Wako Pure Chem. Co. Ltd. (Japan); 20×90 mm) with 75% MeOH containing 0.05M AgNO$_3$. The collected eluent was partitioned with CHCl$_3$ three times, and the CHCl$_3$ fractions were collected and dried using anhydrous Na$_2$SO$_4$ and then filtered. The filtrate was evaporated under reduced pressure to afford Compound 1 as a colorless oil (98.5 mg).

In the above isolation and purification steps, the presence of Compound 1 and Compound 2 in each fraction was followed and confirmed by an intense blue color developed in a reaction of 2,6-dichloroquinon-4-chloroimide (resolved in 85% methanol) and ammonia on thin-layer chromatography using toluene:chloroform:acetone (55:26:19 v/v) as a developing solvent. Compound 3 was chromatographed using toluene:chloroform:acetone (29:32:39 v/v) as a developing solvent.

Example 2

Structural Determination of the Present Capsaicinoid-like Substances

Spectroscopic analyses of the present compounds were performed with the following apparatuses.

$^1$H-NMR (399.65 MHz, CDCl$_3$) and $^{13}$C-NMR (100.40 MHz, CDCl$_3$) spectra (TMS as an internal standard) were recorded on a JEOL alpha-400 instrument. IR spectra were recorded on a Hitachi 270-50 infrared spectrophotometer, and UV spectra were recorded on a Jasco UVIDEC 660 spectrophotometer. HRMS spectra were recorded on a JEOL JMS-700 apparatus.

Identification of Compound 1

Spectral data of Compound 1 obtained with the above analytical means were as follows.

HRMS m/z z(M$^+$): Calcd. (C$_{18}$H$_{26}$O$_4$): 306.1831 Found: 306.1798.

IR $\nu_{max}$ (film) cm$^{-1}$: 3450, 1740, 1615, 1610, 1520, 1470, 1435, 1275, 1160, 1120, 1035, 970, 850, 815, 795, 560.

UV$_{max}$ (MeOH) nm: 280 ($\epsilon$: 2400), 231 ($\epsilon$: 6200).

$^1$H-NMR and $^{13}$C-NMR spectra:

These data are shown in Tables 1 and 2 below, respectively.

The molecular formula of Compound 1 was determined as C$_{18}$H$_{26}$O$_4$ by HRMS measurement. The IR spectrum showed a hydroxyl absorption (3450 cm$^{-1}$) and an ester carbonyl absorption (1735 cm$^{-1}$). The $^1$H-NMR spectrum showed three aromatic protons ($\delta$6.90 d, 6.86 dd, and 6.87 d), and these coupling constants and patterns indicated a typical 1-, 2-, and 4-substituted phenyl group. The phenyl group gave rise to the signals of $\delta$146.5, 145.8, 128.0, 122.0, 114.3 and 111.2 in $^{13}$C-NMR data. In $^1$H-NMR data, two olefinic methine protons ($\delta$5.37 dd and 5.30 dt) coupled to each other with 15.6 Hz indicated the presence of an ethylenic moiety of trans configuration. A methoxyl group ($\delta$3.90 s) and an isopropyl group ($\delta$0.95 d, 0.95 d, and 2.21 oct) were observed in $^1$H-NMR data.

As shown in Table 2, the $^{13}$C-NMR spectrum of Compound 1 was extremely similar to that of authentic capsaicin only except for a methylene carbon at the C-7' position ($\delta$43.5 of capsaicin and $\delta$66.3 of Compound 1). $^1$H-NMR spectrum was also similar to that of capsaicin. However, a chemical shift value of the methylene protons ($\delta$5.03, s) of Compound 1 was different from that of the C-7' position of capsaicin. These NMR signals of the methylene of Compound 1 indicated the existence of a methylene group caught between a phenyl group and oxygen of an ester linkage. These results have suggested that the structure of Compound 1 has an ester moiety instead of an amide moiety of capsaicin.

Furthermore, it has suggested that Compound 1 has the same acyl residue as capsaicin, i.e., (E)-8-methyl-6-nonenoyl group, because $^1$H- and $^{13}$C-NMR spectrum data for the acyl group of Compound 1 agreed excellently with those of capsaicin.

Therefore, it has been concluded that the structure of Compound 1 is 4-hydroxy-3-methoxy-benzyl (E)-8-methylnonenoate as shown in Formula I, and this novel Compound 1 was named "capsiate."

Identification of Compound 2

Spectral data of Compound 2 obtained with the above analytical means were as follows.

HRMS m/z (M$^+$): Calcd. (C$_{18}$H$_{28}$,O$_4$): 308.1987. Found: 308.2008.

IR $\nu_{max}$ (film) cm$^{-1}$: 3450, 1740, 1615, 1610, 1520, 1470, 1435, 1275, 1160, 1120, 1035, 970, 850, 815, 795, 560.

Uv$_{max}$ (MeOH) nm: 279 ($\epsilon$: 3700), 231 ($\epsilon$: 8700).

$^1$H- and $^{13}$C-NMR spectral data: These data are shown in Tables 1 and 2 below, respectively.

The molecular formula of Compound 2 was determined as C$_{18}$H$_{28}$O$_4$ by HRMS measurement. The IR spectral datum of Compound 2 was similar to that of Compound 1. It was therefore presumed that compound 2 has structural resemblance to Compound 1. $^1$H- and $^{13}$C-NMR data of Compound 2 were also similar to those of Compound 1. In the $^{13}$C-NMR spectrum of 2, however, the presence of two alkanic methylene carbons ($\delta$27.2 and 38.9) instead of two olefinic methine carbons of 1 (C-6 and C-7) was observed. The $^1$H-NMR datum of Compound 2 also showed no signals of olefinic protons such as observed in Compound 1. These results suggested the structure of Compound 2 to be a 6,7-dihydro derivative of Compound 1, i.e., 4-hydroxy-3-methoxybenzyl 8-methylnonanoate.

Chemical Synthesis of Compound 2

A mixture of 500 mg (2.9 mmol) of 8-methylnonanoic acid and 3.5 g (2.9 mmol) of thionyl chloride was stirred magnetically overnight at a room temperature under drying with CaCl$_2$. After evaporation under reduced pressure, brown oil was obtained. The oil was added dropwise into 5 mL pyridine solution of 893 mg (5.8 mmol) of vanillyl alcohol (Aldrich Chem. Co. Inc. (Milwaukee, Wis.)). The mixture was stirred magnetically at 0° C. for 2 hours. After the addition of water and 2N-HCl to acidify, the mixture was partitioned with 30 mL each of ethylacetate three times, and the ethylacetate fractions collected were washed with water, dried using anhydrous Na$_2$SO$_4$ and filtered. The filtrate was evaporated under reduced pressure to afford a residue. The residue was chromatographed on silica gel (Silica gel 60 Merck; 36×60 mm). The fraction eluted with n-hexane/ ethylacetate (90:10) gave a colorless oil (2,329 mg, 36.8% yield).

It was revealed that IR spectrum data, $^1$H- and $^{13}$C-NMR spectrum data of the thus synthesized compound were completely the same as those of Compound 2. It has therefore confirmed that Compound 2 is 4-hydroxy-3-methoxybenzyl 8-methylnonanoate, and this novel Compound 2 was named "dihydrocapsiate."

Compound 3 was identified as vanillyl alcohol based on the comparison of the above spectra data between Compound 3 and an authentic reagent.

| Position | Capsaicin* $\delta$ (J, Hz) | 1 $\delta$ (J, Hz) | 2 $\delta$ (J, Hz) |
|---|---|---|---|
| 2 | 2.19, t (7.6) | 2.33, t (7.6) | 2.33, t (7.6) |
| 3 | 1.65, quint (7.6) | 1.63, quint (7.6) | 1.63, quint (7.6) |
| 4 | 1.38, quint (7.6) | 1.37, quint (7.6) | 1.25, m |
| 5 | 1.98, q (7.0) | 1.97, q (6.8) | 1.30, m |
| 6 | 5.30, dt (15.6, 6.0) | 5.30, dt (15.6, 6.4) | 1.25, m |
| 7 | 5.37, dd (15.6, 6.0) | 5.37, dd (15.6, 6.0) | 1.13, q (6.5) |
| 8 | 2.20, oct (6.8) | 2.21, oct (6.8) | 1.50, m |
| 9 | 0.95, d (6.8) | 0.95, d (6.8) | 0.85, d (6.8) |
| 10 | 0.95, d (6.8) | 0.95, d (6.8) | 0.85, d (6.8) |
| 2' | 6.79, d (1.2) | 6.87, d (1.5) | 6.87, d (1.5) |
| 5' | 6.85, d (7.6) | 6.90, d (8.3) | 6.90, d (8.3) |
| 6' | 6.74, dd (7.6, 1.2) | 6.86, dd (8.3, 1.5) | 6.86, dd (8.3, 1.5) |
| 7' | 4.33, d (5.6) | 5.03, s | 5.03, s |
| OMe | 3.85, s | 3.90, s | 3.90, s |
| OH | 5.87, s | 5.64, s | 5.63, s |

*Other signal: NH $\delta$ 5.84 (br t, J = 5.6 Hz)

TABLE 2

| Position | Capsaicin $\delta$ | 1 $\delta$ | 2 $\delta$ |
|---|---|---|---|
| 1 | 172.9 | 173.7 | 173.8 |
| 2 | 36.7 | 34.3 | 34.4 |
| 3 | 25.3 | 24.5 | 25.0 |
| 4 | 29.3 | 29.1 | 29.5 |
| 5 | 32.2 | 32.1 | 29.2 |
| 6 | 126.5 | 126.5 | 27.2 |

TABLE 2-continued

| Position | Capsaicin δ | 1 δ | 2 δ |
|---|---|---|---|
| 7 | 138.1 | 138.1 | 38.9 |
| 8 | 31.0 | 31.0 | 27.9 |
| 9 | 22.7 | 22.6 | 22.6 |
| 10 | 22.7 | 22.6 | 22.6 |
| 1' | 130.3 | 128.0 | 128.0 |
| 2' | 110.7 | 111.2 | 111.3 |
| 3' | 146.9 | 146.5 | 146.5 |
| 4' | 145.2 | 145.8 | 145.8 |
| 5' | 114.4 | 114.3 | 114.4 |
| 6' | 120.7 | 122.0 | 122.0 |
| 7' | 43.5 | 66.3 | 66.3 |
| OMe | 55.9 | 55.9 | 55.9 |

Example 3
Immunopotentiating Activity of the Present Capsaicinoid-like Substances The immunopotentiating activity of the present capsaicinoid-like substances was examined by observing their effect on the antibody production of hybridomas.

The present capsaicinoid-like substances obtained in Example 1 (20.5 mg) was mixed with ethyl acetate (66 μl) to give 1N solution. The resulting solution (8 μl) was resolved into a serum-free ITES ERDF medium containing insulin (5 μg/ml), transferrin (35 μg/ml), ethanol amino (20 μM) and selenium (2.5 nM) to give 200 μM solution. By using this solution, culture media containing the present capsaicinoid-like substances in various concentrations were prepared, and the following hybridomas were cultured in these media. A culture medium containing capsaicin was used as a control.

TABLE 3

| Hybridoma | Antibody Production |
|---|---|
| H8 | Human monoclonal antibody (IgM) |
| S97 | Human monoclonal antibody (IgG) |

Figure 2:
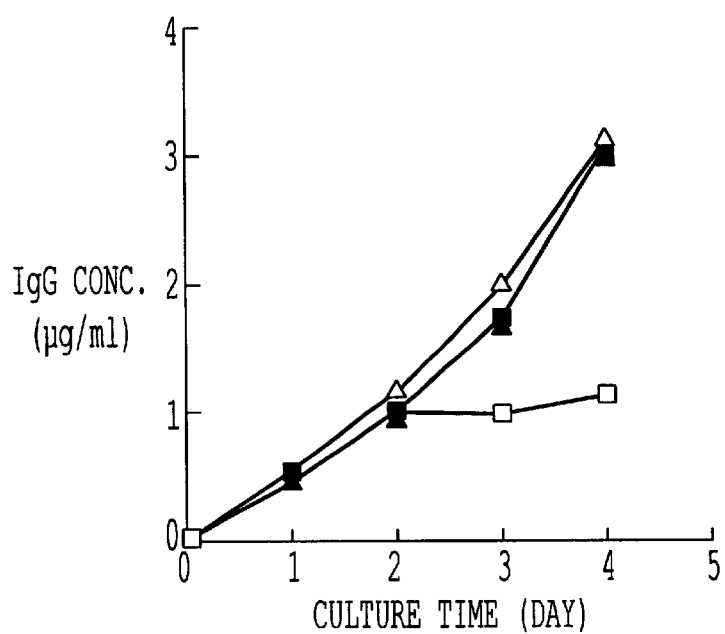
Figure 3:
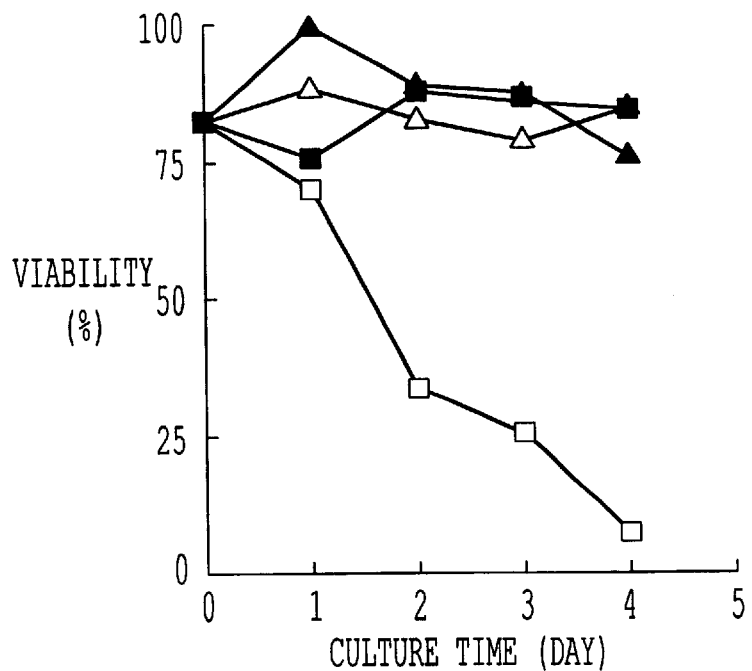

The results shown in FIG. 1, FIG. 2 and FIG. 3 demonstrate that the capsaicinoid-like substances (designaed as "CLS-B" in the figures) increased the production of IgM and IgG by the hybridomas more effectively than capsaicin.

Further, FIG. 3 shows that the capsaicinoid-like substances have an extremely lower cytotoxicity than capsaicin.

Example 4
Energy Metabolism-enhancing Activity of the Present Capsaicinoid-like Substances Energy metabolism-enhancing activity of the present capsaicinoid-like substances was also examined.

Figure 4:
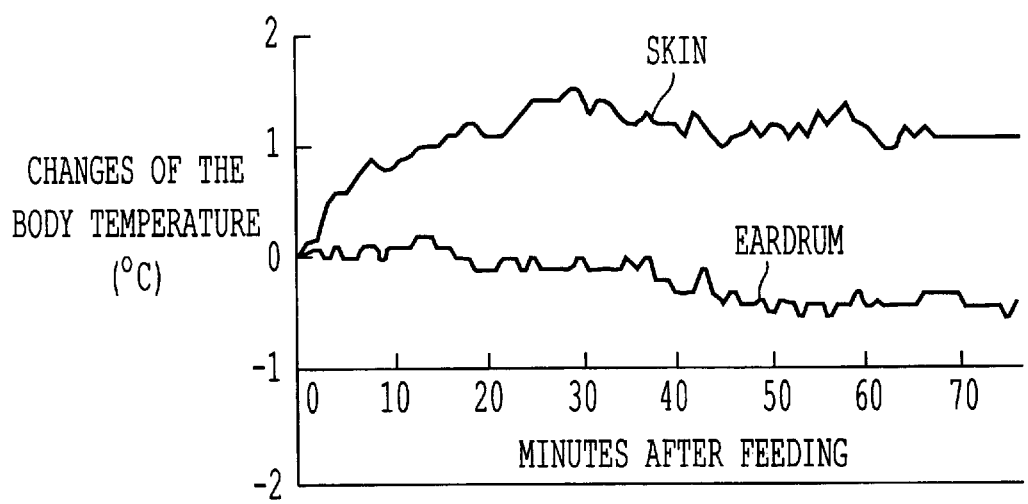

The dried and pulverized material of "CH-19 sweet" (ca. 3 g) was wrapped with a medical wafer and eaten by a subject. Seen from the results in FIG. 4, the temperature of skin rose by 1.4° C. about 30 min after intake. On the other hand, the temperature of eardrum decreased gradually by 0.3° C. about 75 min after intake.

In this feeding experiment, no remarkable languidness was observed in the subjet, contrary to the case of feeding of a cultivated pungent variety, *Capsium annuum* var. *parvoacuninatum*. The above results mean that the dried and pulverized material of "CH-19 sweet" has a temperature-rising activity (energy metabolism-enhancing activity) without causing any stimulation.

Further, mice were fed with the present capsaicinoid-like substances to observe the energy metabolism-enhancing activity.

Figure 5:
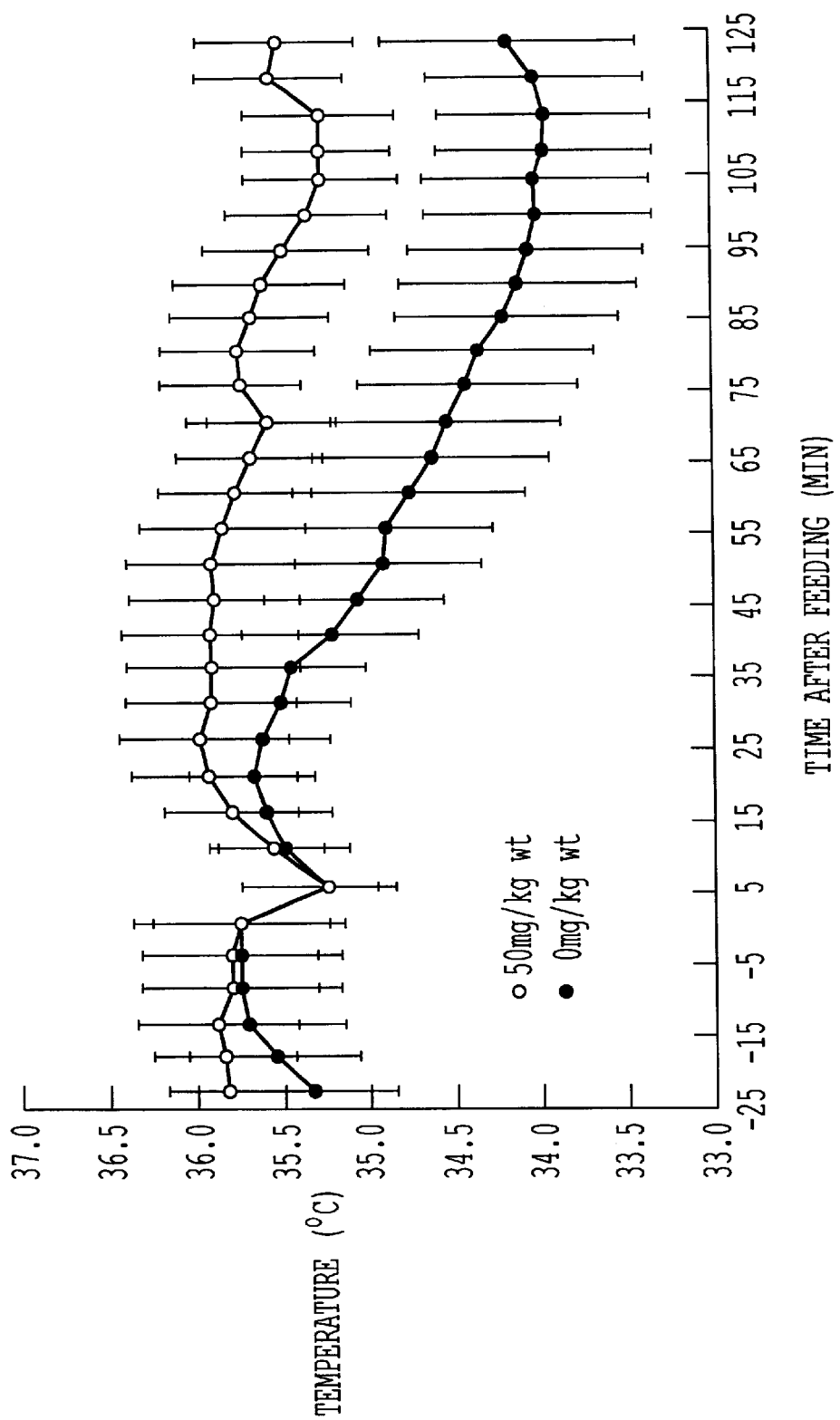

As seen from the results in FIG. 5, the temperature of the mice fed with the present capsaicinoid-like substances became higher than that of non-fed mice.

Example 5
Food Composition Comprising the Present Capsaicinoid-like Substances

The food compositions comprising the present capsaicinoid-like substances were prepared according to a known method in the art. All the numerical values below are represented as parts by weight.

TABLE 4

| Chocolate: | |
|---|---|
| Sugar | 45.56 |
| Cocoa mass | 20.00 |
| Total lipid pulverized milk | 16.50 |
| Cocoa butter | 16.50 |
| Lecithin | 0.40 |
| Vanilla flavor | 0.04 |
| The dried and pulverized material of "CH-19 sweet" | 1.00 |
| (Total) | 100.00 |

TABLE 5

| Sport drink: | |
|---|---|
| Orange juice concentrate | 0.200 |
| Sugar | 1.8 |
| High fructose corn syrup (F-55) | 5.5 |
| Citric acid | 0.14 |
| Salt | 0.08 |
| Sodium citrate | 0.07 |
| Potassium chloride | 0.04 |
| Calcium phosphate | 0.013 |
| Sodium glutamate | 0.004 |
| Magnesium chloride | 0.003 |
| Ascorbic acid | 0.1 |
| Cloudy | 0.1 |
| Emulsifying flavor | 0.01 |
| Essence | 0.2 |
| Capsaicinoid-like substances (*) | 0.05 |
| Remainder (Water) | |

The capsaicinoid-like substances(*) used in the above sport drink was an oleoresin containing about 50 ppm of the capsaicinoid-like substances and prepared as follows.

After fresh fruits (1.00 kg) of CH-19 sweet had been freeze-dried, its seeds and calyces were removed, and the residue was the extracted with 1.5 L each of ethylacetate three times by use of a Universal Homogenizer (Nihon Seiki Seisakusho, Japan). The ethylacetate extract was evaporated under reduced pressure to distill out ethylacetate and to afford the oleoresin.

TABLE 6

| Royal jelly drink: | |
|---|---|
| High fructose corn syrup (F-55) | 12.5 |
| Purified honey | 11.0 |
| Raw royal jelly | 4.5 |
| Garlic extract | 0.2 |
| Litchi Extract | 0.3 |
| Citric acid | 0.1 |
| Poly dextrose | 4.0 |
| Natural caffeine | 0.08 |
| Ascorbic acid | 0.5 |
| Vitamin B1 hydrochloride | 0.02 |

TABLE 6-continued

| Royal jelly drink: | |
| --- | --- |
| Vitamin B2 phosphate | 0.01 |
| Vitamin B hydrochloride | 0.03 |
| Nicotinamide | 0.04 |
| Cloudy | 0.1 |
| Essence | 0.4 |
| Capsaicinoid-like substances (Formula III or IV) | 0.001 |
| Remainder (Water) | |

TABLE 7

| Retort pouched adzuki beans gruel: | |
| --- | --- |
| Brown rice "Koshihikari" | 4.20 |
| Milled rice "Koshihikari" | 4.90 |
| Adzuki produced in Hokkaido | 1.60 |
| Sugar | 0.50 |
| Salt | 0.10 |
| Fruit of "CH-19 sweet" | 2.0 |
| Remainder (Water) | |

Adzuki beans were selected, soaked in water overnight and then weighed. Fresh fruits of "CH-19 sweet" were soaked in hot water for 5 min for blanching and finely cut into pieces of about 5 mm in size. These cut pieces and other ingredients were packed into an aluminum pouch to a final weight of 300 g, and subjected to retort treatment at 120° C. for 35 min.

The same experiment as in Example 4 using the above retort food indicated the temperature-rising at body surface, showing that "CH-19 sweet" per se has energy metabolism-enhancing activity.

Advantages of the Invention

The novel capsaicinoid-like substances with an ester linkage have been obtained by the present invention. Unlike the well-known capsaicin, the present substances have no pungency and substantially no cytotoxicity, and they may be widely used as food additives.

The present capsaicinoid-like substances were confirmed to have activities of enhancing energy metabolism and potantiating an immune system. Seeing that other physiological activities such as anti-fatigability and anti-obesity are now being found in them, the present capsaicinoid-like substances are very useful as food additives and pharmaceutical ingredients.

What is claimed:

1. A capsaicinoid-like substance represented by the following general formula:

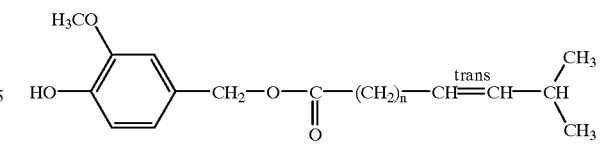

2. The capsaicinoid-like substance according to claim 1 wherein the value "n" is 3, 4 or 5.

3. The capsaicinoid-like substance according to claim 2 wherein the value "n" is 4.

4. A capsaicinoid-like substance represented by the following general formula:

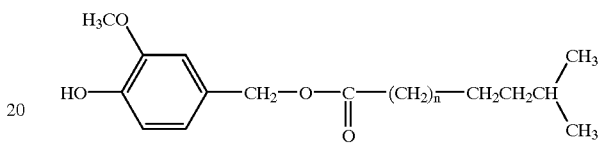

5. The capsaicinoid-like substance according to claim 4 wherein the value "n" is 3, 4 or 5.

6. The capsaicinoid-like substance according to claim 5 wherein the value "n" is 4.

7. A food composition comprising the capsaicinoid-like substance of claim 1.

8. A food composition comprising a non-pungent fixed variety of pepper, "CH-19 Sweet", its dried and pulverized material or its extract with ethyl acetate or ethanol.

9. A food composition according to claim 7, that has an immunopotentiating activity.

10. A food composition according to claim 7, that has an enhancing activity of energy metabolism.

11. A pharmaceutical composition comprising the capsaicinoid-like of claim 1.

12. A food composition comprising the capsaicinoid-like substance of claim 4.

13. A food composition according to claim 8, that has an immunopotentiating activity.

14. A food composition according to claim 8, that has an enhancing activity of energy metabolism.

15. A pharmaceutical composition comprising the capsaicinoid-like substance of claim 4.

* * * * *

UNITED STATES PATENT AND TRADEMARK OFFICE
CERTIFICATE OF CORRECTION

PATENT NO. : 6,333,421 B1
DATED : December 25, 2001
INVENTOR(S) : Yazawa et al.

It is certified that error appears in the above-identified patent and that said Letters Patent is hereby corrected as shown below:

Title page,
Item [86], PCT, information should read:
-- [86]  PCT No.:        PCT/JP99/00999
         § 371 Date:     Sept. 26, 2000
         § 102(e) Date:  Sept. 26, 2000 --

Signed and Sealed this

Twenty-third Day of August, 2005

JON W. DUDAS
*Director of the United States Patent and Trademark Office*